(12) United States Patent  (10) Patent No.: US 6,712,821 B2
Gabbay  (45) Date of Patent: Mar. 30, 2004

(54) STERNUM CLOSURE APPARATUS AND METHOD FOR HELPING MAINTAIN A SPACE BETWEEN PARTS OF THE STERNUM

(76) Inventor: Shlomo Gabbay, #1 Randall Dr., Short Hills, NJ (US) 07078

( * ) Notice: Subject to any disclaimer, the term of this patent is extended or adjusted under 35 U.S.C. 154(b) by 50 days.

(21) Appl. No.: 10/194,654

(22) Filed: Jul. 12, 2002

(65) Prior Publication Data

US 2004/0010256 A1 Jan. 15, 2004

(51) Int. Cl.[7] .............................................. A61B 17/08
(52) U.S. Cl. ............................ 606/71; 606/72; 606/76; 606/213
(58) Field of Search .............................. 606/69, 70, 71, 606/72, 73, 74, 76, 213, 215, 216

(56) References Cited

U.S. PATENT DOCUMENTS

| | | |
|---|---|---|
| 4,279,248 A | 7/1981 | Gabbay |
| 4,730,615 A | 3/1988 | Sutherland et al. |
| 4,802,477 A | 2/1989 | Gabbay |
| 4,813,416 A | 3/1989 | Pollak et al. |
| 4,944,753 A | 7/1990 | Burgess et al. |
| 5,318,566 A | 6/1994 | Miller |
| 5,330,489 A | 7/1994 | Green et al. |
| 5,339,870 A | 8/1994 | Green et al. |
| 5,356,412 A | 10/1994 | Golds et al. |
| 5,356,417 A | 10/1994 | Golds et al. |
| 5,462,542 A | 10/1995 | Alesi, Jr. |
| 5,722,976 A | 3/1998 | Brown |
| 5,810,854 A | 9/1998 | Beach |
| 5,928,231 A | 7/1999 | Klein et al. |
| 6,007,538 A | 12/1999 | Levin |
| 6,033,429 A | 3/2000 | Magovern |
| 6,045,572 A | 4/2000 | Johnson et al. |
| 6,051,007 A | 4/2000 | Hogendijk et al. |
| 6,217,580 B1 | 4/2001 | Levin |
| 6,228,087 B1 | 5/2001 | Fenaroli et al. |
| 6,302,899 B1 | 10/2001 | Johnson et al. |

Primary Examiner—David O. Reip
(74) Attorney, Agent, or Firm—Tarolli, Sundheim, Covell & Tummino L.L.P.

(57) ABSTRACT

An apparatus (10) maintains a desired distance between two parts (5, 6) of a severed sternum of a patient. The apparatus (10) includes an elongate member (20), such as a plastic or surgical steel plate, and an element (60) for securing the elongate member (20) to each of the two parts (5, 6) of the severed sternum. The elongate member (20) has longitudinal edges (32, 34) dimensioned and configured to space apart the two parts (5, 6) of the severed sternum the desired distance. When implanted, the two parts (5, 6) of the severed sternum engage the longitudinal edges (32, 34) of the elongate member (20) to maintain the desired distance between such parts.

31 Claims, 6 Drawing Sheets

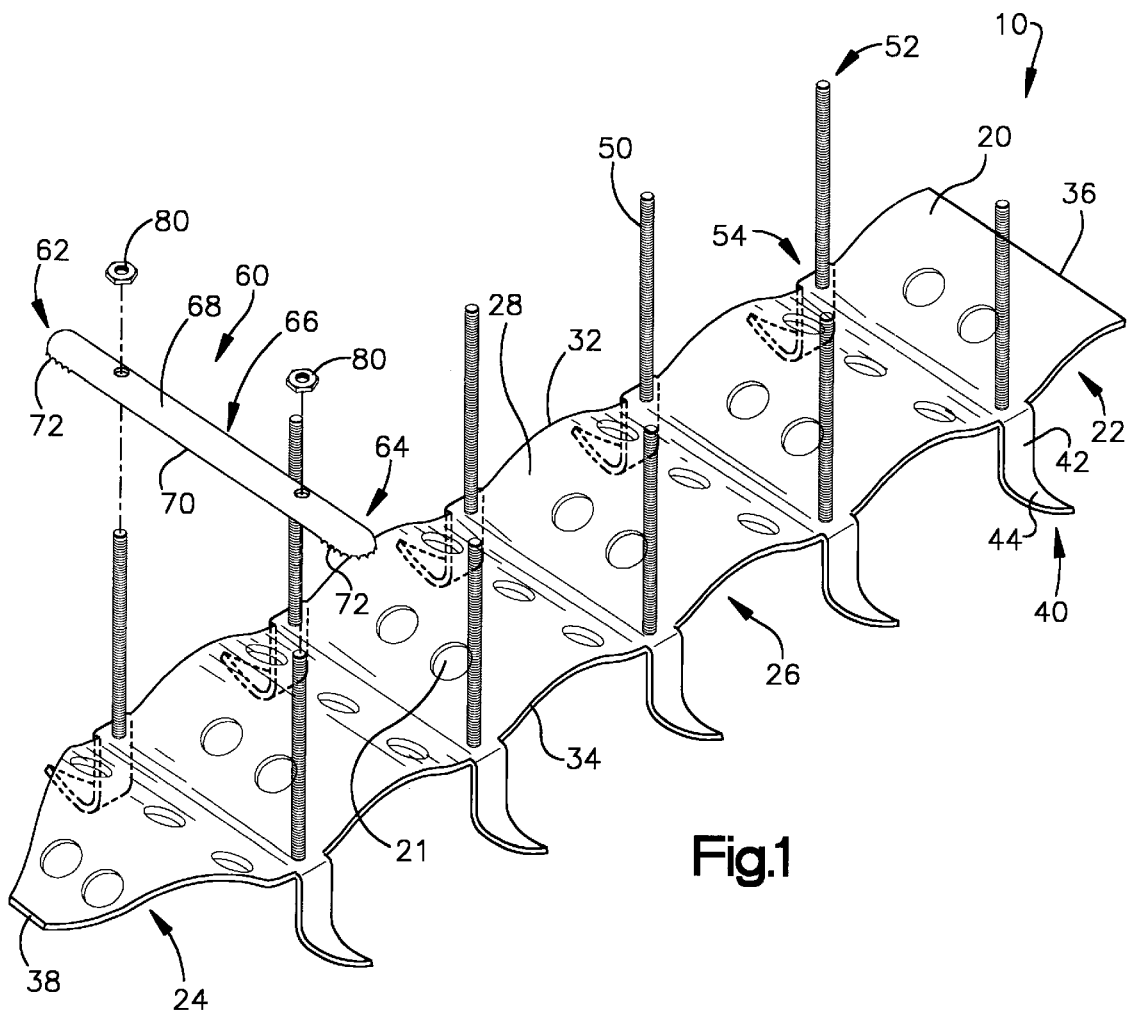
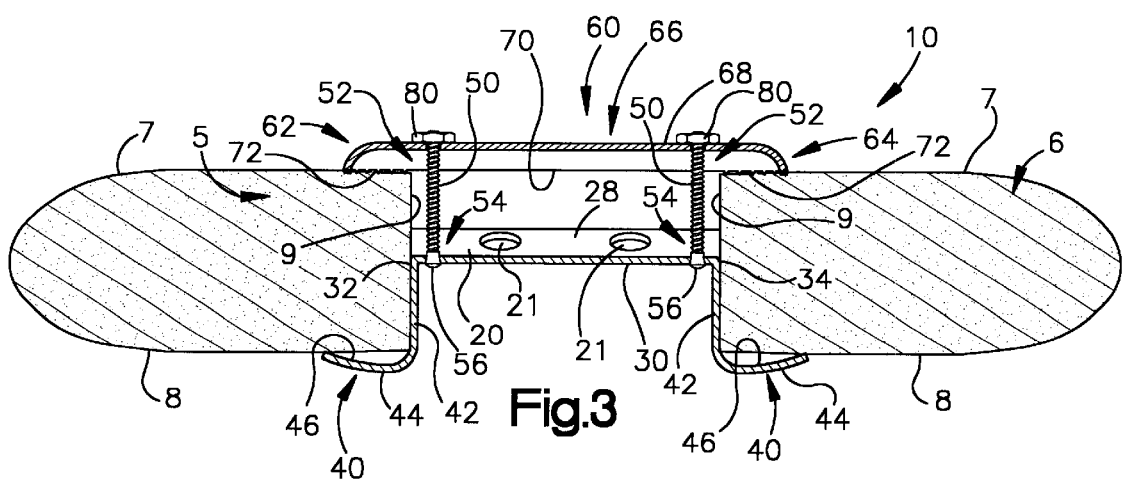

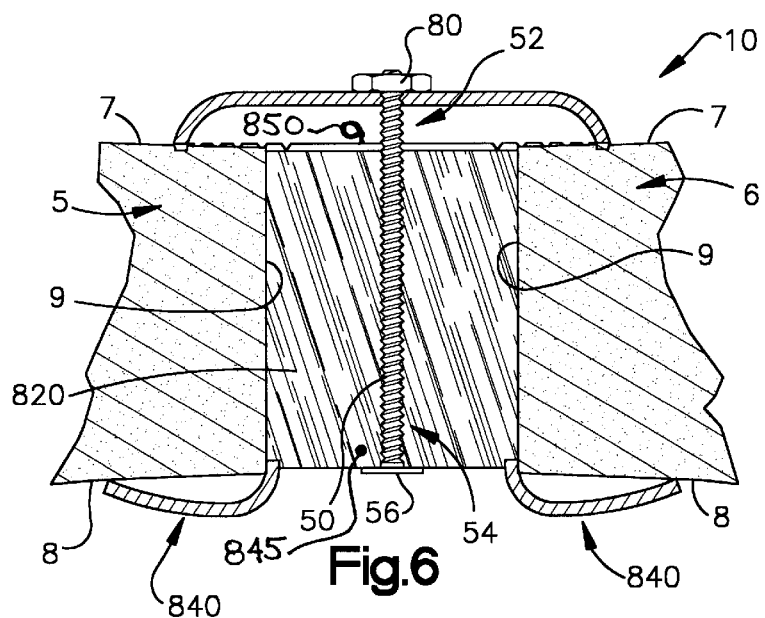
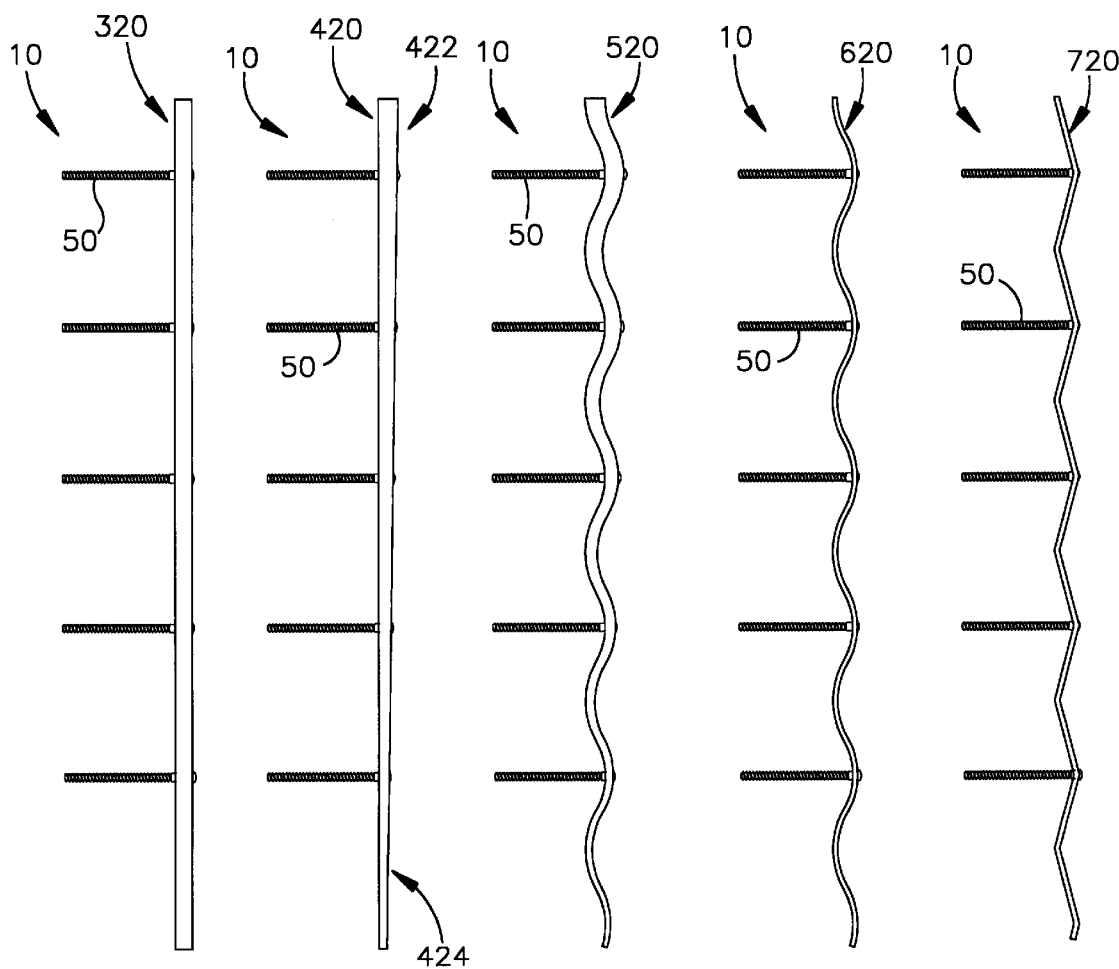
Fig.6  Fig.7  Fig.8  Fig.9  Fig.10  Fig.11

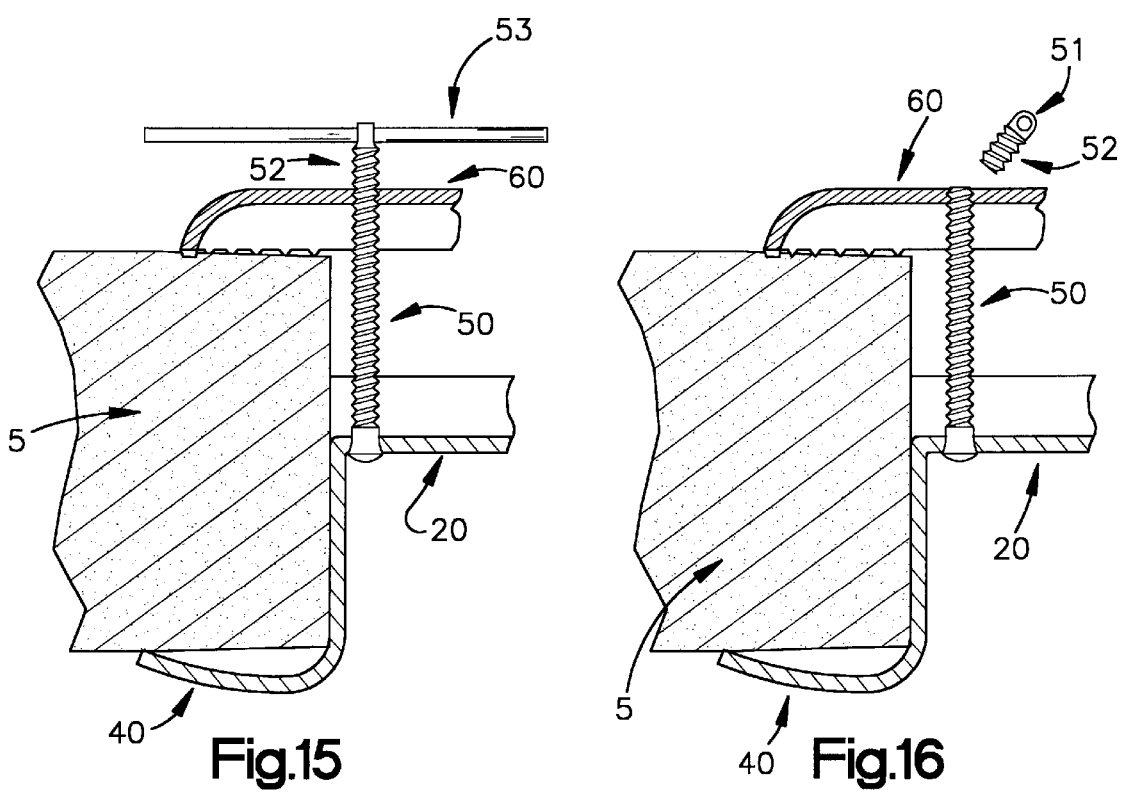

STERNUM CLOSURE APPARATUS AND METHOD FOR HELPING MAINTAIN A SPACE BETWEEN PARTS OF THE STERNUM

TECHNICAL FIELD

The present invention is directed to a surgical device and method, and more particularly, to a sternum closure device that helps maintain a predetermined space between parts of the severed sternum after closure.

BACKGROUND OF THE INVENTION

Thousands of open-heart operations are performed in the United States each year. In order to perform most of them, the chest is opened through a mid-line sternotomy (the sternum of the chest bone is longitudinally split with an electrical saw). After the procedure is complete, the sternum is closed by a conventional method such as stainless steel wire or a clamping mechanism. However, the heart and other organs often become edematous, swollen, and generally larger than their original size. As a result, while closing the sternum and after the closure, the pressure exerted by the sternum over the enlarged organs may cause post-procedure complications such as low blood pressure, arythmias, and possibly even fatality.

Further, one conventional clamping closure device typically does not involve the perforation of the sternum for insertion of the stainless steel wire. The large needle utilized to perforate the sternum for insertion of the wire can cause major bleeding complications, infections, and needless destruction of the sternal tissue. This conventional clamping device achieves easy and strong closure of the sternum without the destruction caused by use of the wire.

SUMMARY OF THE INVENTION

The following presents a simplified summary of the invention in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

In accordance with one aspect of the present invention, an apparatus maintains a predetermined distance between two parts of a severed sternum of a patient, such as after closure of the severed sternum. The apparatus includes an elongate spacer member, such as a plate formed of plastic, surgical steel, or a bone-substitute material, and an element for securing the elongate member to each of the two parts of the severed sternum. The elongate member has a length approximately equal to the length of the sternum. The elongate member has longitudinally extending edges dimensioned and configured to space apart the two parts of the severed sternum the predetermined distance (e.g., the width of the plate defines the predetermined distance). The vertical surfaces of the severed sternum abut the longitudinally extending edges of the elongate member and are fastened there by the securing element to maintain the predetermined distance.

In accordance with another aspect of the present invention, an apparatus maintains a desired space between a vertical surface of a first member and a vertical surface of a second member (e.g., parts of the severed sternum). The apparatus includes an elongate spacer plate, at least one shaft fastened to the elongate plate, and a retaining element for securing the elongate plate to the first member. The elongate plate has a first end portion and a second end portion opposite the first end portion. The elongate plate further has a first longitudinally extending lateral edge portion and a second longitudinally extending lateral edge portion opposite the first lateral edge portion. The elongate plate further has upper and lower opposed surfaces. The shaft extends away from the upper surface of the elongate plate. The retaining element engages the shaft such that the first member is fixed between the retaining element and a projection of the elongate plate. The retaining element is adapted to engage an upper surface of the first member. The projection of the elongate plate engages a lower surface of the first member. The projection has a first part and a second part. The first part of the projection extends downward away from the lower surface of the elongate plate. The second part of the projection extends laterally away from the first lateral edge portion of the elongate plate and the first part of the projection. The elongate plate can thus be fixed in abutting engagement with the vertical surface of the first member and in engagement with the upper and lower surfaces of the first member, such that the first member is clamped between the retaining element and the projection of the elongate plate.

In accordance with still another aspect of the present invention, a method maintains a post-closure space between opposite parts of a longitudinally severed sternum of a patient. The method includes implanting an elongate spacer member between the opposite parts of the longitudinally severed sternum, such as following an open-heart procedure. The severed sternum is closed such that vertical surfaces of the opposite parts of the longitudinally severed sternum each engage the elongate member. The elongate member can then be secured to the opposite parts of the severed sternum such that a lateral dimension of the elongate member provides the post-closure space for enlarging the volume of the patient's chest cavity to mitigate pressure on the organs of the patient.

BRIEF DESCRIPTION OF THE DRAWINGS

The foregoing and other features of the present invention will become apparent to one skilled in the art to which the present invention relates upon consideration of the following description of the invention with reference to the accompanying drawings.

FIG. 1 is a schematic perspective view of an apparatus in accordance with one feature of the present invention.

FIG. 3 is a schematic sectional view taken along line 3—3 in FIG. 2.

FIG. 6 is a schematic sectional view similar to FIG. 3 showing yet another aspect of the present invention.

FIG. 7 is a schematic longitudinal sectional view of one aspect of the apparatus of FIG. 1.

FIG. 8 is a schematic longitudinal sectional view of another aspect of the apparatus of FIG. 1.

FIG. 9 is a schematic longitudinal sectional view of still another aspect of the apparatus of FIG. 1.

FIG. 10 is a schematic longitudinal sectional view of yet another aspect of the apparatus of FIG. 1.

FIG. 11 is a schematic longitudinal sectional view of still another aspect of the apparatus of FIG. 1.

FIG. 15 is a schematic view of another aspect of part of the apparatus of FIG. 1 in a third installation position.

FIG. 16 is a schematic view of still another aspect of part of the apparatus of FIG. 1 in a fourth installation position.

DESCRIPTION OF THE EXAMPLE EMBODIMENTS

Figure 2:
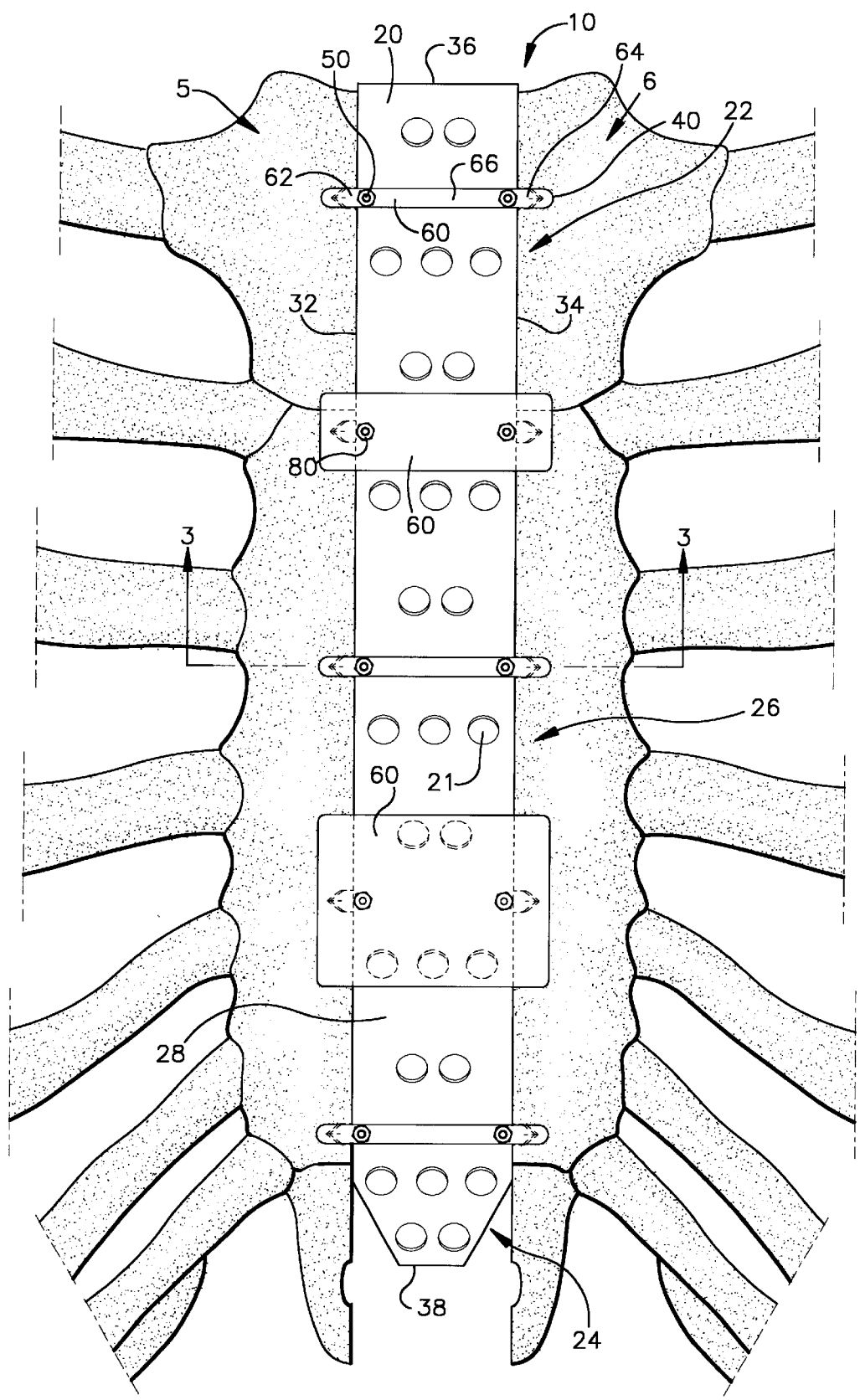
FIG. 2 is schematic orthogonal view of the apparatus of FIG. 1 implanted within a patient.

In accordance with one aspect of the present invention, as viewed in FIGS. 1–3, an apparatus 10 maintains a predetermined distance between the parts 5, 6 of a severed sternum, such as following an open-heart procedure and closure of the sternum. The apparatus 10 includes an elongate plate-like spacer member 20, a plurality of threaded shafts 50, and securing means that include a plurality of elongate retainers 60.

In the example shown in FIGS. 1–3, the elongate member 20 is generally planar and generally rectangular. The elongate member 20 has an upper portion 22, an opposite lower portion 24, and a central portion 26 interposed between the upper and lower portions. The lower portion 24 may be tapered to approximate the contour of a patient's sternum, which facilitates insertion into the patient. The elongate member 20 has an anterior surface 28 (e.g., facing outward from the patient when implanted) and an opposite posterior surface 30 (e.g., facing the patient's organs when the elongate member 20 is implanted in the patient). The anterior and posterior surfaces 28, 30 define a first longitudinal edge portion 32, a second opposite longitudinal edge portion 34, a third upper edge portion 36, and a fourth opposite lower edge portion 38. Because the first and second edge portions 32, 34 are tapered at the lower portion 24, the fourth edge portion 38 is shorter than the third edge portion 36.

It will be understood and appreciated that, the apparatus can be provided in a variety of sizes, each having a different lateral dimension (or width) so as to enable corresponding increases in the volume of the patient's chest cavity proportional to its width. For example, the distance between side edges 32 and 34 can vary, for example, from about 5 mm to about 0.3 mm to about 100 mm so as to allow for a wide range of increased lung capacity.

The elongate member 20 further includes a plurality of foot-like projections 40 extending posteriorly and laterally away from the first longitudinal edge portion 32 and the second longitudinal edge portion 34. Each L-shaped projection 40 has a first part 42 and a second part 44. Each first part 42 extends in a posterior direction away from (e.g., substantially perpendicular to a plane extending through the member 20) its associated longitudinal edge portion 32, 34 and the posterior surface 30 of the elongate member 20. Each second part 44 extends generally laterally away from its associated first part 42 and laterally away from its associated longitudinal edge portion 32 or 34. Each second part 44 has an anterior surface 46 for engaging a posterior surface 8 of the parts 5, 6 of the severed sternum. The second parts 44 can be configured to grippingly engage the respective posterior surfaces 8 of the sternum parts 5, 6 when the member 20 is implanted, such as shown in FIG. 3.

A plurality of threaded shafts 50 extends outwardly from the anterior surface 28 of the elongate member 20 (e.g., five shown along each side in FIG. 1). The shafts 50 each have a first anterior end 52 and a second opposite posterior end 54. The posterior end 54 of each shaft 50 has a flange 56 for engaging the posterior surface 30 of the elongate member 20. Each shaft 50 extends away from the flange 56 through an opening in the elongate member 20 and away from the anterior surface 28 of the elongate member. The flange 56 can be fixed or rotatable about its longitudinal axis relative to the member 20 in accordance with aspects of the present invention.

In the particular example of FIGS. 1–3, each pair of shafts 50 has an associated elongate retainer 60 for securing the elongate member 20 between the parts 5, 6 of the severed sternum. Each elongate retainer 60 has a first lateral part 62, a second lateral part 64, and a third central part 66 interposed between the first and second parts. The first and second lateral parts 62, 64 extend laterally to each side of the elongate member 20. The central part 66 of each elongate retainer 60 has a pair of openings through which the corresponding pair of shafts 50 extends. Each elongate retainer 60 has a rounded anterior surface 68 and a planar, generally oval posterior surface 70. The posterior surfaces 70 of the first and second lateral parts 62, 64 have triangular teeth 72 projecting in a posterior direction. The teeth 72 penetrate the anterior surfaces 7 of the parts 5, 6 of the severed sternum for maintaining the position of the elongate retainer 60 against the anterior surfaces.

As viewed in FIG. 2, the elongate retainer 60 may have varying widths, depending upon how much protection is required for the gap between the parts 5, 6 of the severed sternum. A single retainer (not shown) may be used extending from the upper sternum to the lower sternum. This single elongated retainer could, for example, totally cover the gap between the parts 5, 6 of the severed sternum.

As viewed in FIG. 3, when the elongate member 20 and the shafts 50 are assembled and placed between the parts 5, 6 of the severed sternum, the vertical surfaces 9 of the parts 5, 6 of the severed sternum are brought into abutment with the longitudinal edge portions 32, 34 of the elongate member 20.

Figure 4:
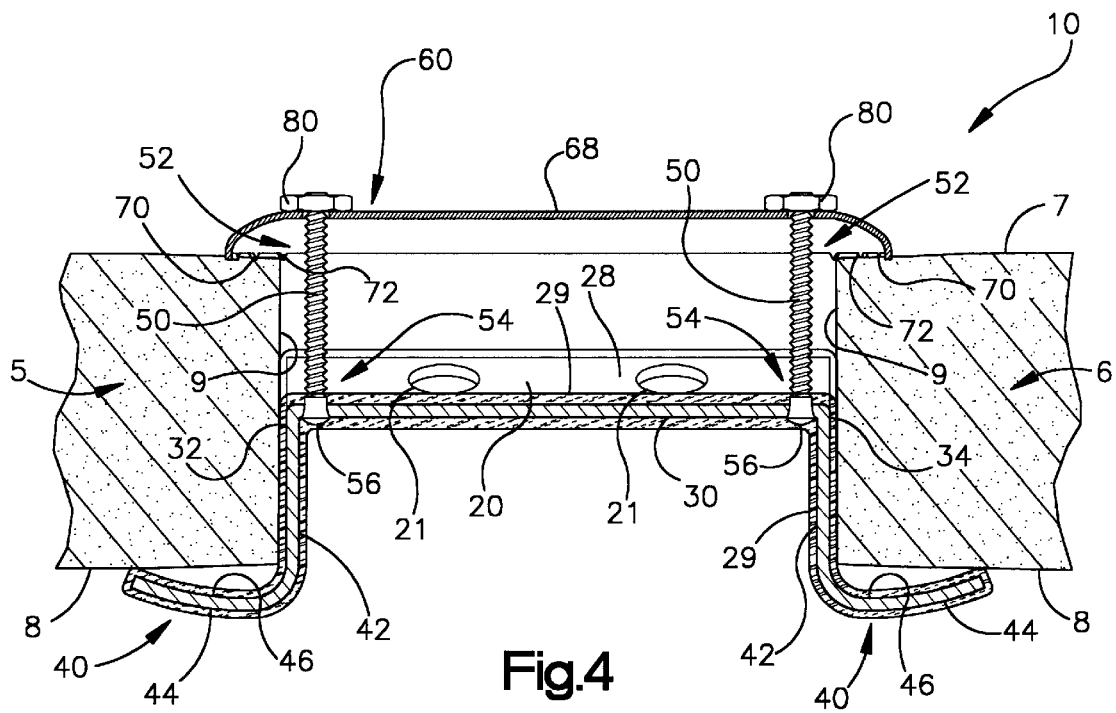
FIG. 4 is a schematic view similar to FIG. 3 in accordance with another aspect of the present invention.

FIG. 4 illustrates another aspect of the apparatus 10. The elongate member 20 is covered with a sheath 29 of natural or synthetic material, such as animal pericardium (e.g., bovine, equine, porcine) or other suitable generally flexible biocompatible material. The pericardium sheath 29, for example, such as has been fixed in a suitable glutaraldehyde solution further can be substantially detoxified tissue. Those skilled in the art will understand and appreciate that a covering of pericardium or other tissue (natural or synthetic) can be used in connection with any of the designs shown and described herein (see, e.g., FIGS. 7–11) as well as can be applied over retaining features (see, e.g., FIGS. 1–6, 13–16).

For example, the pericardium layer can include one or more sheets of a NO-REACT® tissue product, such as an elongated pericardial patch, which is commercially available from Shelhigh, Inc., of New Jersey. The NO-REACT® tissue helps improve the biocompatibility of the resulting apparatus 10, thereby mitigating the likelihood of a patient rejecting the implanted prosthesis. Animal pericardium, when treated in this manner, also becomes substantially elastic and resilient as well as resists calcification. As a result of its improved biocompatibility, the animal pericardium 29 can facilitate healing and absorption around the implanted apparatus 10.

Figure 5:
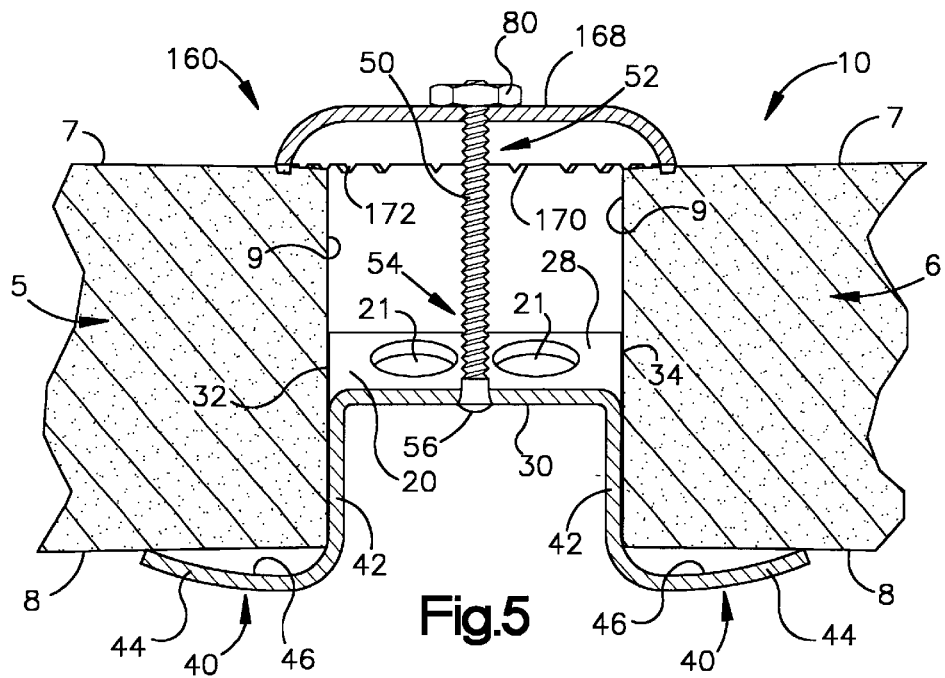
FIG. 5 is a schematic view similar to FIG. 3 in accordance with still another aspect of the present invention.

As viewed in FIG. 5, the elongate retainer 60 may alternatively be replaced by a retainer 160. The retainer 160 may be disk-shaped and have only a single opening for receiving a single shaft 50. This type of retainer 160 is particularly useful when the elongate member 20 has a narrow lateral dimension (e.g., when a small gap between the parts 5, 6 of the severed sternum is desired). The disk-shaped retainer 160 has a rounded anterior surface 168 and a planar, generally circular posterior surface 170. The posterior surface 170 has triangular teeth 172 for penetrating the anterior surfaces 7 of the parts 5, 6 of the severed sternum (similar to the elongate retainer 60).

As viewed in FIG. 6, an elongate member 820 may be formed of a bone substitute material in accordance with an aspect of the present invention. The thickness of the member 820 can approximate the thickness of the parts 5, 6 of the sternum. For example, the elongate member 820 may be any natural or synthetic bone substitute material. The material can be implanted between the parts 5, 6 of the sternum, for example, an injectable paste, a moldable putty, or a pre-hardened block of material. Projections 840 of a suitable material extend laterally from the elongate member 820 to help secure the parts 5, 6 of the severed sternum in a manner similar to that described herein. An adhesive material (not shown) also could be used to help secure the member 820 between the parts 5, 6 of the sternum.

Additionally, a flexible saw 845 can be located within or below the elongate bone substitute material member 820. For example, the saw 845 is formed of an abrasive wire (e.g., a Gigli saw) having a length greater than that of the member 820. Ends 850 of the saw 845 (only one of which is shown in the cross-sectional view of FIG. 6) can include respective loops to facilitate grasping. Thus, the ends 850 of the saw 845 can be brought around the ends 36 and 38 of the member 820 and/or ribs and secured at the upper side of the member, such as near or to a retaining element. This can be done by simply suturing the ends 850 to adjacent tissue or to adjacent retaining elements. Alternatively, the ends could be clamped between the member 820 and one of the sternum parts 5, 6.

The saw 845 substantially facilitates re-opening the patient's chest. For example, the ends 850 of saw 845 can be removed from their generally secure location and then reciprocated. The reciprocation of the saw 845 results in causing saw to cut through the member 820. Those skilled in the art will understand and appreciate that such a saw also could be located in other locations to facilitate reopening, such as between the projections 840 and respective sternum parts 5, 6, in which reciprocation might cause the saw to cut through part of the sternum or ribs. It further will be understood and appreciated that such a saw could also be utilized in conjunction with any of the other configurations of apparatuses shown and described herein in accordance with an aspect of the present invention.

Those skilled in the art will understand and appreciated that other suitable types of generally rigid biocompatible material (e.g., natural or synthetic) also can be utilized in accordance with the present invention to provide a member 820 for spacing apart parts 5, 6 of the sternum, which also may approximate the thickness of the sternum, in accordance with an aspect of the present invention. For example, two (or more) spaced apart elongate members can be used in juxtaposition to approximate the thickness of the parts 5, 6 of the sternum and to laterally space apart such sternum parts.

As viewed in FIGS. 1–5 and 9–11, the elongate member 20 has a wave-like shape in order to increase the stiffness of the elongate member 20 against external loads. The elongate member 20 also may have openings 21 for facilitating tissue growth around the elongate member. Alternatively, the elongate member 20 may have no openings to further increase the stiffness of the elongate member.

As viewed in FIG. 7, the anterior and posterior surfaces of an elongate member 320 may define a single plane with a uniform thickness. As viewed in FIG. 8, the thickness of an elongate member 420 may vary from the upper end portion 422 to the lower end portion 424 (decrease shown).

FIG. 9 illustrates an elongate member 520 with a wave-like shape and a variable thickness. FIG. 10 illustrates an elongate member 620 with a wave-like shape and a uniform thickness. FIG. 11 illustrates an elongate member 720 with a zigzag wave shape and a uniform thickness. Which of these features is utilized, and in what combination, in a particular situation may be determined by cost, desired stiffness, gap desired between the parts 5, 6 of the severed sternum, size of the patient, etc.

Figure 12:
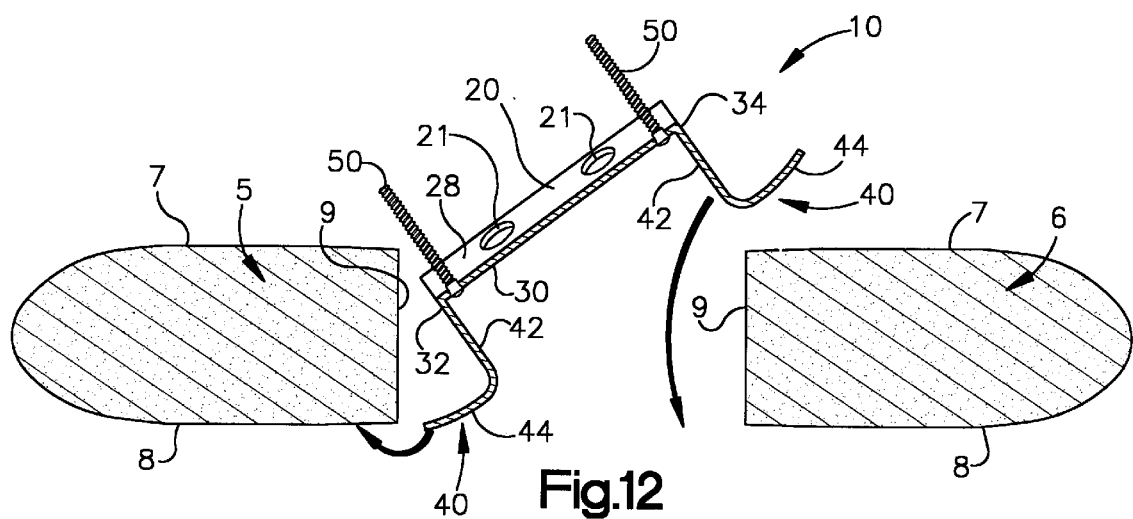
FIG. 12 is a schematic view showing a method of positioning the apparatus of FIG. 1 within a patient.

By way of illustration, as viewed in FIG. 12, the elongate member 20 and connected shafts 50 may be inserted between the vertical surfaces 9 of the parts 5, 6 of the severed sternum by rotating the elongate member 20 about its longitudinal axis and inserting one longitudinal edge portion 32 or 34 in a posterior direction such that the projections 40 are deep enough within the patient such that the anterior surfaces 46 of the second parts 44 may engage the posterior surfaces 8 of the parts 5, 6 of the severed sternum. The opposite longitudinal edge portion 34 or 32 of the elongate member 20 may then be inserted to that same depth within the patient. The vertical surfaces 9 of the opened sternum may be moved toward the elongate member 20 in any known manner, such as by the use of a sterna approximator or other closure mechanism.

Figures 13, 14:
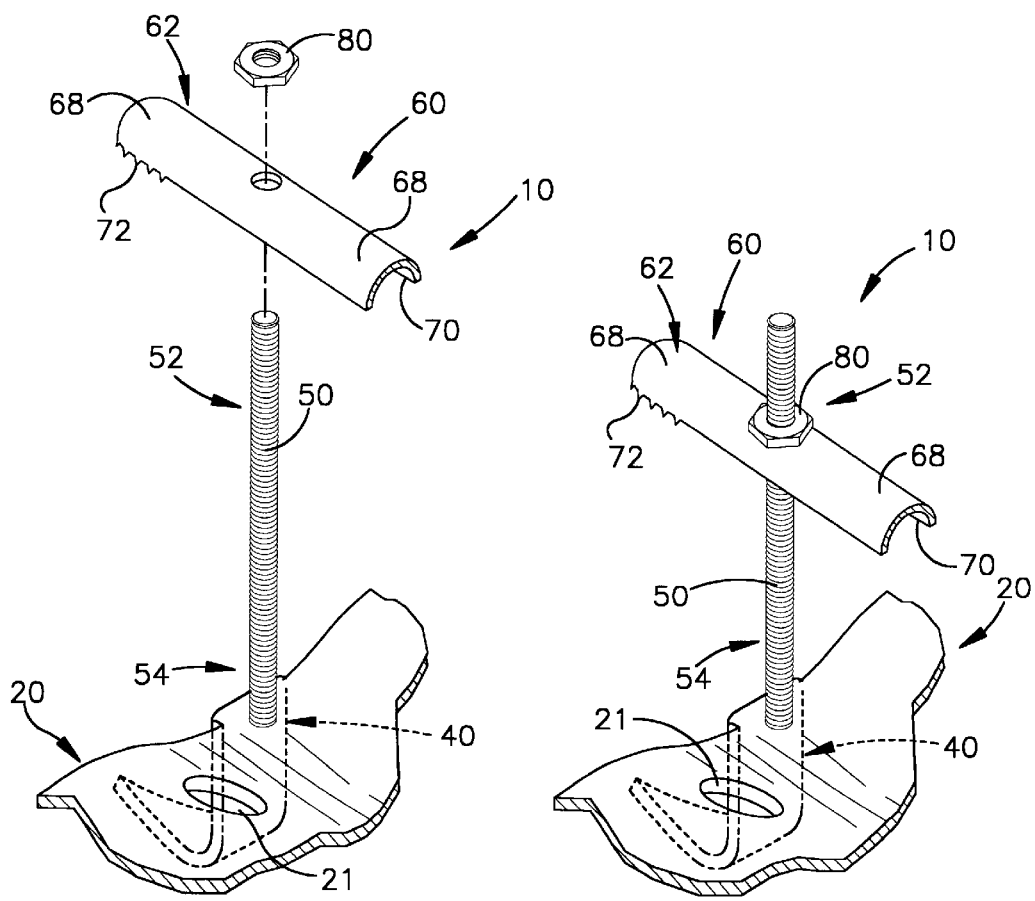
FIG. 13 is a schematic view of part of the apparatus of FIG. 1 in a first installation position.
FIG. 14 is a schematic view of part of the apparatus of FIG. 1 in a second installation position.

FIGS. 13 and 14 illustrate an example of how to position an elongate retainer 60 along the respective threaded shaft 50 according to one aspect of the present invention. The elongate retainer 60 is positioned such that the shaft 50 extends through the openings of the elongate retainer and away from the anterior surface 28 of the elongate retainer. A threaded fastener 80, such as a nut, may be threaded onto each shaft 50 so that a posterior surface of each fastener engages the anterior surface 68 of its associated elongate retainer 60. The fasteners 80 are then tightened so that the posterior surfaces 70 of the first and second lateral parts 62, 64 of each elongate retainer 60, and the triangular teeth 72, engage and penetrate the anterior surfaces 7 of the parts 5, 6 of the severed sternum. The tightening of the fasteners 80 against the anterior surface 68 of the elongate retainer 60 also forces the anterior surfaces 46 of the second parts 44 of the projections 40 against the posterior surfaces 8 of the parts 5, 6 of the severed sternum.

The elongate member 20 is thus secured against lateral movement by the vertical surfaces 9 of the parts 5, 6 of the severed sternum and against anterior/posterior movement by the projections 40 of the elongate member 20 and the elongate retainers 60. The elongate member 20 is further secured against upward/downward movement by a clamping force provided by the fasteners 80 and also the teeth 72 of the elongate retainers 60 penetrating the anterior surfaces 7 of the parts 5, 6 of the severed sternum. After each fastener 80 is tightened sufficiently, the upper portion 52 of each corresponding shaft 50 that extends above the fastener may be cut off and discarded, as shown in FIG. 3.

As viewed in FIGS. 15 and 16, for an alternative method of securing the apparatus 10 to the parts 5, 6 of the sternum, each shaft 50 may have a loop 51 at its first anterior end 52. A rod 53 may pass through the loop of the shaft 50, thereby allowing the shaft to be rotated. With this method, the opening in the retainer 60 would have threads so that no separate fastener 80 is required and the shafts 50 would be free to rotate relative to the elongate member 20. After closure and clamping of the parts 5, 6 of the sternum, the portions of the first anterior end 52 of the shaft 50 (including the loops 51, if present) that extend above the retainer 60 may be cut off and discarded (FIG. 16). The cut edge of the shaft 50 may then be finished so that no sharp edges remain. Those skilled in the art will understand and appreciate that such a method of securing can be utilized in connection with any of the retainers and elongate members shown and described herein.

An alternative aspect of the present invention may include the use of absorbable surgical polymers for the elongate member as well as the retainers. Such polymers are well known in the art. With this aspect, the patient's body may absorb all or part of the implants after a period sufficient to permit natural healing. If desired, portions of the apparatus 10 that require greater strength may be made of metal or plastic set into the absorbable polymer.

For example, the portions of the retainers 60, 160 that engage threads of the shaft 50 may be constructed of metal or plastic. Similarly, the shaft 50 itself may also be metal or plastic. Additionally, it may be easy to reopen the sternum as part or all of the apparatus 10 will have been absorbed and need not be removed, thus simplifying the procedure.

In view of the foregoing structural and functional aspects, those skilled in the art will understand and appreciate how the various types of apparatuses in accordance with an aspect of the present invention can be utilized to help maintain a desired space between parts of a longitudinally severed sternum of a patient. By way of example, the desired space can be maintained by implanting an elongate member (e.g., the member 20, 320, 420, 520 620, 720, 820) between opposite parts 5, 6 of the longitudinally severed sternum. The member can be inserted in a manner described with respect to FIG. 12, although those skilled in the art will appreciate other ways to insert the member according to an aspect of the present invention. Once in place, the parts 5, 6 of the longitudinally severed sternum can be permitted to close toward each other, such that the opposite parts 5, 6 of the longitudinally severed sternum each engage the elongate member. At this point, the elongate member can be secured to the opposite parts 5, 6 of the severed sternum such that a lateral dimension of the elongate member 20 provides the desired post-closure space.

The securing of the apparatus relative to the patient's sternum further may include threading a fastener on to a threaded shaft, the threaded shaft extending from the elongate member 20, and the step of securing parts 5, 6 of the severed sternum between projections 40 of the elongate member 40 and a retainer element 60. The method may further include the step of severing a portion of a threaded shaft 50 subsequent to the securing step.

It will be appreciated that the space provides the patient with an enlarged chest cavity (e.g., the apparatus causes an increase in volume for the patient's chest). The increase in volume thus can to facilitate healing of the patient, such as after having undergone a surgical procedure to one or more organs or body parts therein and, in turn, reduce the likelihood of re-operation. Additionally, such a procedure can be utilized in conjunction with or even as an alternative to a lung reduction procedure. By spacing apart the sternum in such a manner, the patient's diaphragm should elevate a significant amount, even without a lung reduction procedure.

Those skilled in the art will understand and appreciate that any combination of elongate members and retainers can be utilized as part of such procedure. Additionally, the apparatus can include an associated flexible saw, such as shown and described with respect to FIG. 6, to facilitate reopening of the sternum after closure, as described herein.

What has been described above includes examples of the present invention. It is, of course, not possible to describe every conceivable combination of components or methodologies for purposes of describing the present invention, but one of ordinary skill in the art will recognize that many further combinations and permutations of the present invention are possible. For example, the retainers may be of a wide variety of configurations and of materials other than those described above. Accordingly, the present invention is intended to embrace all such alterations, modifications and variations that fall within the spirit and scope of the appended claims.

Having described the invention, the following is claimed:

1. An apparatus for maintaining a predetermined distance between two parts of a severed sternum of a patient, the apparatus comprising:

an elongate member having a length approximately equal to the length of the sternum, the elongate member having longitudinal edges dimensioned and configured to extend between and space apart the two parts of the severed sternum the predetermined distance; and means for securing the elongate member to each of the two parts of the severed sternum.

2. The apparatus as set forth in claim 1, wherein the securing means further comprises an elongate retainer for engaging both parts of the severed sternum.

3. The apparatus as set forth in claim 1, further comprising at least one threaded shaft that extends outwardly from the elongate member for interconnecting the elongate member and the securing means.

4. The apparatus of claim 3, the at least one threaded shaft further comprising a plurality of threaded shafts arranged near the longitudinal edges of the elongate member.

5. The apparatus of claim 3, the at least one threaded shaft being rotatable about a longitudinal axis thereof.

6. The apparatus of claim 1, the securing means further comprising a retainer having a threaded aperture dimensioned and configured for threading engagement with the at least one threaded shaft.

7. The apparatus as set forth in claim 1, the securing means further comprises a generally disk-shaped retainer for engaging at least one of the two parts of the severed sternum.

8. The apparatus as set forth in claim 7, further comprising a threaded shaft for interconnecting the elongate member and the disk-shaped retainer.

9. The apparatus as set forth in claim 8, further comprising a fastener for threadedly engaging the threaded shaft to urge the elongate member toward the retainer.

10. The apparatus as set forth in claim 1, wherein the elongate member has apertures extending at least partially therethrough to facilitate tissue growth around the elongate member.

11. The apparatus of claim 1, further comprising a sheath of biologically compatible tissue material that covers the elongate member.

12. The apparatus as set forth in claim 11, wherein the sheath is a substantially detoxified biological tissue material.

13. The apparatus as set forth in claim 1, wherein the elongate member has projections for engaging the posterior surfaces of the parts of the severed sternum.

14. The apparatus of claim 13, the projections extend generally transversely relative to a generally planar body portion of the elongate member and terminating in outwardly extending feet dimensioned and configured for engaging the posterior surfaces of the parts of the severed sternum.

15. The apparatus of claim 1, further comprising a length of a flexible saw associated with the elongate member to facilitate reopening of the sternum of a patient post implantation of the apparatus.

16. An apparatus for helping maintain a space between adjacent parts of a patient's skeletal structure, the apparatus comprising:

an elongate body portion having a first end portion and a second end portion opposite the first end portion, the body portion further having a first lateral edge portion and a second lateral edge portion opposite the first lateral edge portion, the body portion further having an upper surface and a lower surface opposite the upper surface;

at least one shaft extending outwardly from the upper surface of the body portion; and a retaining element for securing the body portion relative to at least one of the adjacent parts, the retaining element being moveable along the shaft to a provide a desired fixed distance between the retaining element and the body portion, the retaining element being adapted to engage an upper surface of the at least one of the adjacent parts of the patient's skeletal structure; and at least one projection extending from the lower surface of the body portion and dimensioned and configured for engaging a lower surface of the at least one of the adjacent parts the patient's skeletal structure.

17. The apparatus of claim 16, the at least one projection further comprises a plurality of projections, each having a first part and a second part adjacent the first part, the first part of the projection extending outwardly from the lower surface of the plate, the second part of the projection extending laterally away from the first part.

18. The apparatus as set forth in claim 16, the retaining element further comprising teeth for gripping an anterior surface of the at least one of the adjacent parts the patient's skeletal structure.

19. The apparatus as set forth in claim 18, wherein the retaining element comprises an elongate member having at least one aperture extending through the retaining element dimensioned and configured to receive the at least one shaft.

20. The apparatus of claim 19, the at least one shaft further comprising at least a pair of shafts, each shaft extending from the upper surface of the body portion near one of the lateral edge portions, the elongate member of the retaining element further comprising a pair of apertures extending therethrough and spaced apart from each other to facilitate receiving a pair of the shafts.

21. The apparatus as set forth in claim 19, the retaining element comprises a disk-shaped member having a generally central aperture dimensioned and configured to receive the at least one shaft.

22. The apparatus as set forth in claim 16, wherein the elongate body portion has a wave-like cross-section in a longitudinal direction for increasing the stiffness of the elongate body portion.

23. The apparatus of claim 16, wherein the at least one shaft is threaded and rotatable about a longitudinal axis thereof.

24. The apparatus of claim 23, wherein the retaining element has a threaded aperture dimensioned and configured for threaded engagement with the at least one shaft.

25. The apparatus of claim 16, wherein the elongate body portion is covered with biologically compatible animal tissue material.

26. The apparatus of claim 16, further comprising a flexible saw associated with the body portion to facilitate reopening of the sternum of a patient post implantation of the apparatus.

27. A method for maintaining a post-closure space of a longitudinally severed sternum of a patient, the method comprising:

positioning an elongate member between opposite parts of the longitudinally severed sternum;

closing the longitudinally severed sternum such that the opposite parts of the longitudinally severed sternum each engages an opposite edge of the elongate member; and securing the elongate member relative to at least one of the opposite parts of the severed sternum such that a lateral dimension of the elongate member provides the post-closure space, thereby providing an increase in volume for the patient's chest cavity.

28. The method as set forth in claim 27, wherein the securing further comprises threading a fastener on to a threaded shaft that extends from the elongate member.

29. The method of claim 27, the securing further comprises threading a retainer on to a rotatable, threaded shaft that extends from the elongate member.

30. The method of claim 27, the securing further comprises securing parts of the severed sternum between laterally extending projections of the elongate member and a retainer element.

31. The method of claim 27, after the closing of the sternum, the method further comprises using a saw associated with the elongate member to reopen the closed sternum.

* * * * *